(12) United States Patent
Azemi

(10) Patent No.: US 8,334,412 B2
(45) Date of Patent: Dec. 18, 2012

(54) PROCESS FOR PREPARING 3-(METHYLTHIO)PROPANAL

(75) Inventor: Takushi Azemi, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/186,206

(22) Filed: Jul. 19, 2011

(65) Prior Publication Data

US 2012/0022295 A1    Jan. 26, 2012

(30) Foreign Application Priority Data

Jul. 20, 2010    (JP) ................................ 2010-162523

(51) Int. Cl.
  *C07C 319/18*    (2006.01)
(52) U.S. Cl. ........................................................ 568/41
(58) Field of Classification Search ............... 568/41
  See application file for complete search history.

(56) References Cited

U.S. PATENT DOCUMENTS

| 5,352,837 | A |   | 10/1994 | Hsu et al. |
| 5,663,409 | A |   | 9/1997 | Blackburn et al. |
| 5,696,282 | A | * | 12/1997 | Shaw et al. .................... 560/152 |
| 6,187,963 | B1 |   | 2/2001 | Etzkorn et al. |
| 7,799,953 | B2 |   | 9/2010 | Shiozaki et al. |

| 2002/0173677 | A1 |   | 11/2002 | Hsu et al. |
| 2006/0030739 | A1 | * | 2/2006 | Dubner et al. .................. 568/63 |
| 2010/0256419 | A1 | * | 10/2010 | Azemi et al. .................... 568/41 |

FOREIGN PATENT DOCUMENTS

| EP | 0 830 341 B1 | 9/2001 |
| EP | 1408029 A1 | 4/2004 |
| EP | 1413573 A1 | 4/2004 |
| JP | 9-501145 A | 2/1997 |
| JP | 11-511119 A | 9/1999 |
| JP | 2004-115461 A | 4/2004 |
| WO | 96/40631 A1 | 12/1996 |

OTHER PUBLICATIONS

Preliminary Search Report and Written Opinion dated Feb. 27, 2012 for French Application No. FR1156577.
Belyakova et al., "Reaction of Unsaturated Nitriles with Hydrosilanes," Russian Journal of General Chemistry, vol. 80, No. 5, 2010, pp. 927-929.
Spanish Communication dated Apr. 12, 2012 for Spanish Application No. 201131231 includes Spanish Search Report dated Apr. 2, 2012.

* cited by examiner

*Primary Examiner* — Johann Richter
*Assistant Examiner* — Pancham Bakshi
(74) *Attorney, Agent, or Firm* — Birch, Stewart, Kolasch & Birch, LLP

(57) ABSTRACT

The present invention provides a process for preparing 3-(methylthio)propanal which can sufficiently decrease the production of high-boiling impurities as a by-product. The process comprises reacting acrolein and methyl mercaptan in the presence of Allylamines (I), Triallylamines (II), and preferably an optional organic acid. The preferred amount of Allylamines (I) is 0.001 to 0.50 mol per 1 mol of Triallylamines (II).

6 Claims, No Drawings

PROCESS FOR PREPARING 3-(METHYLTHIO)PROPANAL

TECHNICAL FIELD

The present invention relates to a process for preparing 3-(methylthio)propanal by reacting acrolein and methyl mercaptan. 3-(Methylthio)propanal is useful as, for example, a synthetic material for preparing methionine.

BACKGROUND ART

A well-known process for preparing 3-(methylthio)propanal by reacting acrolein and methyl mercaptan is carried out in the presence of pyridine or a derivative thereof (See, for example, Patent References 1 to 3).

PRIOR ART DOCUMENTS

[Patent Reference 1] JP 2004-115461 A
[Patent Reference 2] JP 11(1999)-511119 T
[Patent Reference 3] JP 9(1997)-501145 T

SUMMARY OF INVENTION

Problems to be Solved by Invention

However, the conventional process mentioned above is not so satisfactory because the process produces high-boiling impurities as a by-product. Thus, the purpose of the present invention is to provide a process for preparing 3-(methylthio)propanal which can sufficiently decrease the production of such high-boiling-impurities.

Means to Solve Problems

The present inventors have extensively studied to reach the above purpose and then have found a new process to solve the above problems. Based upon the new findings, the present invention has been completed.

In detail, the present invention provides a process for preparing 3-(methylthio)propanal which comprises reacting acrolein and methyl mercaptan in the presence of a compound of Formula (I):

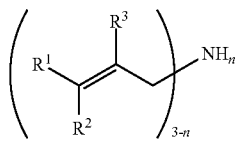

wherein $R^1$, $R^2$ and $R^3$ are independently selected from the group consisting of hydrogen atom and an alkyl group having 1 to 4 carbon atoms, and n is an integer of 1 or 2 and a compound of Formula (II):

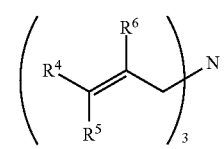

wherein $R^4$, $R^5$, and $R^6$ are independently selected from the group consisting of hydrogen atom and an alkyl group having 1 to 4 carbon atoms.

Effects of Invention

The present invention can prepare 3-(methylthio)propanal while sufficiently decreasing the production of high-boiling impurities which generate as a by-product.

DESCRIPTION OF EMBODIMENTS

In the present invention, the following two compounds are used as a catalyst: a compound of Formula (I):

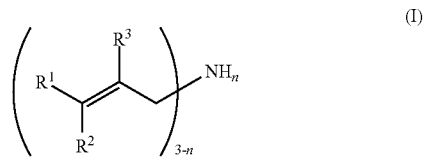

wherein $R^1$, $R^2$ and $R^3$ are independently selected from the group consisting of hydrogen atom and an alkyl group having 1 to 4 carbon atoms, and n is an integer of 1 or 2 [hereinafter, optionally referred to as "Allylamines (I)"] and a compound of Formula (II):

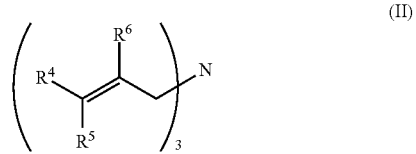

wherein $R^4$, $R^5$, and $R^6$ are independently selected from the group consisting of hydrogen atom and an alkyl group having 1 to 4 carbon atoms [hereinafter, optionally referred to as "Triallylamines (II)"].

The present invention can sufficiently decrease the production of high-boiling impurities by using Allylamines (I) and Triallylamines (II) together as a catalyst. When used together, the production of high-boiling impurities can be decreased more effectively than when using either Allylamines (I) or Triallylamines (II) alone. The alkyl group having 1 to 4 carbon atoms in the compound of Formula (I) or Formula (II) includes methyl group, ethyl group, n-propyl group, iso-propyl group, n-butyl group, s-butyl group, and t-butyl group.

Allylamines (I) used herein include, for example, diallylamines [i.e. the compounds of Formula (I) wherein n is 1] such as diallylamine, di(2-butenyl)amine, di(3-methyl-2-butenyl)amine, di(2-pentenyl)amine and di(2-hexenyl)amine, as well as mono-allylamines [i.e. the compounds of Formula (I) wherein n is 2] such as allylamine, 2-butenylamine, (3-methyl-2-butenyl)amine, 2-pentenylamine, and 2-hexenylamine. A mixture of 2 or more of the above-listed compounds may also be used if necessary. Among Allylamines (I), diallylamine and allylamine are preferred.

Triallylamines (II) used herein include, for example, triallylamine [i.e. the compound of Formula (I) wherein $R^4$, $R^5$, and $R^6$ are all hydrogen atoms], tri(2-butenyl)amine, tri(3-methyl-2-butenyl)amine, tri(2-pentenyl)amine, and tri(2-hexenyl)amine. A mixture of 2 or more of the above-listed compounds may also be used if necessary. Among Triallylamines (II), triallylamine is preferred.

The present invention can decrease the production of high-boiling impurities more effectively when an organic acid is used together with Allylamines (I) and Triallylamines (II). The organic acid used herein includes, for example, carboxylic acids such as aliphatic monocarboxylic acids (e.g. formic acid, acetic acid, propionic acid, octanoic acid, acrylic acid, trichloroacetic acid, and trifluoroacetic acid); aliphatic polycarboxylic acids (e.g. oxalic acid, succinic acid, and adipic acid); aromatic monocarboxylic acids (e.g. phenylacetic acid, benzoic acid, cinnamic acid, and thiophenecarboxylic acid); and aromatic polycarboxylic acids (e.g. phthalic acid); as well as sulfate monoesters and sulfonic acids. Among the organic acids, carboxylic acids are preferred and acetic acid is more preferred.

The amount of methyl mercaptan used herein is generally about equimolar to acrolein. In order to reduce the odor of 3-methylthiopropanal, it is preferred to use acrolein slightly more than methyl mercaptan. More preferably, 0.95 to 0.99 mol of methyl mercaptan is used per 1 mol of acrolein.

Although the amount of Allylamines (I) used herein may be optionally fixed, the amount is preferably 0.001 to 0.50 mol, and more preferably 0.010 to 0.25 mol per 1 mol of Triallylamines (II). In addition, when two or more compounds are used as Allylamines (I) or Triallylamines (II) as defined above, the total amount of Allylamines (I) can be fixed in the above-mentioned range per 1 mol of the total amount of Triallylamines (II).

Although the amount of Triallylamines (II) used herein may be optionally fixed, the amount is preferably 0.1 to 2.0 mmol per 1 mol of methyl mercaptan. When an organic acid is further present in the reaction, the amount of Triallylamines (II) is preferably 0.01 to 1.0 mol, and more preferably 0.2 to 0.7 mol per 1 mol of the organic acid. In addition, when two or more compounds are used as Triallylamines (II) as defined above, the total amount thereof can be fixed in the above-mentioned range.

Methods of mixing acrolein, methyl mercaptan, Allylamines (I) and Triallylamines (II) should not be limited to a particular method. Exemplified methods are, mixing a mixture of acrolein, Allylamines (I) and Triallylamines (II) with methyl mercaptan; mixing a mixture of methyl mercaptan, Allylamines (I) and Triallylamines (II) with acrolein; supplying acrolein, methyl mercaptan, and a mixture of Allylamines (I) and Triallylamines (II) separately to the reaction system; and supplying acrolein, methyl mercaptan, Allylamines (I), and Triallylamines (II) separately to the reaction system. Among the methods, it is preferred to supply acrolein, methyl mercaptan, and a mixture of Allylamines (I) and Triallylamines (II) separately to the reaction system. Furthermore, in case that an organic acid is used, it is preferred to mix the organic acid with a mixture of Allylamines (I) and Triallylamines (II) beforehand, and then mix the prepared mixture with acrolein and methyl mercaptan. It is especially preferred to supply acrolein; methyl mercaptan; and a mixture of Allylamines (I), Triallylamines (II) and the organic acid separately to the reaction system.

The reaction of the present invention may be carried out in a batch manner or in a continuous manner, but a continuous manner is preferred from the viewpoint of productivity. The reaction temperature is generally −10 to 100° C., preferably 0 to 80° C. The reaction time is generally about 10 minutes to about 24 hours. In a continuous manner, the reaction time indicates a mean staying time, while in a batch manner, it indicates a reacting time per batch. The reaction may be carried out under reduced, ordinary, or increased pressure. In addition, other ingredients like inert solvents may also be supplied to the reaction if necessary.

The post-treatment of the reaction mixture containing 3-(methylthio)propanal may be performed by a method selected optionally from well-known methods. For example, 3-(methylthio)propanal can be isolated and purified from the reaction mixture by distilling the mixture.

EXAMPLES

Hereinafter, some examples of the present invention are illustrated, but the present invention should not be construed to be limited thereto.

Example 1

The reaction was carried out in a batch manner in a reactor equipped with a stirrer and each supply-inlet for acrolein, methyl mercaptan, and a mixture of Allylamines (I)/Triallylamines (II)/acetic acid. The reactor was charged with 122 g of acrolein (purity: 92 wt %, 2.00 mol), 93.4 g of methyl mercaptan (1.94 mol), and 0.172 g of a mixture of triallylamine/diallylamine/acetic acid (molar ratio: 1/0.014/3.7, respectively; i.e. triallylamine 0.48 mmol/diallylamine 0.0066 mmol/acetic acid 1.76 mmol). The reaction mixture was stirred at 25-55° C. for 30 minutes, and the resultant solution was distilled (20 torr, 70-120° C.) to obtain 3-(methylthio)propanal. The weight of the concentrated residue (i.e. high-boiling oligomer) was weighed to find that it was 1.5 wt % per the reaction solution.

Example 2

The reaction was carried out in the same manner as Example 1 except that 0.174 g of a mixture of triallylamine/diallylamine/acetic acid (molar ratio: 1/0.054/3.7, respectively; triallylamine 0.48 mmol/diallylamine 0.026 mmol/acetic acid 1.76 mmol) was used instead of 0.172 g of the mixture of triallylamine/diallylamine/acetic acid (molar ratio: 1/0.014/3.7, respectively). The resultant residue (i.e. high-boiling oligomer) was 1.3 wt %.

Example 3

The reaction was carried out in the same manner as Example 1 except that 0.178 g of a mixture of triallylamine/diallylamine/acetic acid (molar ratio: 1/0.14/3.7, respectively; i.e. triallylamine 0.48 mmol/diallylamine 0.066 mmol/acetic acid 1.76 mmol) was used instead of 0.172 g of the mixture of triallylamine/diallylamine/acetic acid (molar ratio: 1/0.014/3.7, respectively). The resultant residue (i.e. high-boiling oligomer) was 1.1 wt %.

Example 4

The reaction was carried out in the same manner as Example 1 except that 0.172 g of a mixture of triallylamine/allylamine/acetic acid (molar ratio: 1/0.023/3.7, respectively; i.e. triallylamine 0.48 mmol/allylamine 0.011 mmol/acetic acid 1.76 mmol) was used instead of 0.172 g of the mixture of triallylamine/diallylamine/acetic acid (molar ratio: 1/0.014/3.7, respectively). The resultant residue (i.e. high-boiling oligomer) was 1.5 wt %.

Example 5

The reaction was carried out in the same manner as Example 1 except that 0.173 g of a mixture of triallylamine/ allylamine/acetic acid (molar ratio: 1/0.046/3.7, respectively; i.e. triallylamine 0.48 mmol/allylamine 0.022 mmol/acetic acid 1.76 mmol) was used instead of 0.172 g of the mixture of triallylamine/diallylamine/acetic acid (molar ratio: 1/0.014/ 3.7, respectively). The resultant residue (i.e. high-boiling oligomer) was 1.0 wt %.

Example 6

The reaction was carried out in the same manner as Example 1 except that 0.178 g of a mixture of triallylamine/ allylamine/acetic acid (molar ratio: 1/0.23/3.7, respectively; i.e. triallylamine 0.48 mmol/allylamine 0.11 mmol/acetic acid 1.76 mmol) was used instead of 0.172 g of the mixture of triallylamine/diallylamine/acetic acid (molar ratio: 1/0.014/ 3.7, respectively). The resultant residue (i.e. high-boiling oligomer) was 1.9 wt %.

Reference Example 1

The reaction was carried out in a batch manner in a reactor equipped with a stirrer and each supply-inlet for acrolein, methyl mercaptan, and a mixture of triallylamine/acetic acid. The reactor was charged with 122 g of acrolein (purity: 92 wt %, 2.00 mol), 93.4 g of methyl mercaptan (1.94 mol), and 0.172 g of a mixture of triallylamine/acetic acid (molar ratio: 1/3.7, respectively; i.e. triallylamine 0.48 mmol/acetic acid 1.76 mmol). The reaction mixture was stirred at 25-55° C. for 30 minutes, and the resultant solution was distilled (20 torr, 70-120° C.) to obtain 3-(methylthio)propanal. The weight of the concentrated residue (i.e. high-boiling oligomer) was weighed to find that it was 2.1 wt % per the reaction solution.

Reference Example 2

The reaction was carried out in a batch manner in a reactor equipped with a stirrer and each supply-inlet for acrolein, methyl mercaptan, and a mixture of diallylamine/acetic acid. The reactor was charged with 122 g of acrolein (purity: 92 wt %, 2.00 mol), 93.4 g of methyl mercaptan (1.94 mol), and 0.198 g of a mixture of diallylamine/acetic acid (molar ratio: 1/1.8, respectively; i.e. diallylamine 0.97 mmol/acetic acid 1.73 mmol). The reaction mixture was stirred at 40-70° C. for 30 minutes, and the resultant solution was distilled (20 torr, 70-120° C.) to obtain 3-(methylthio)propanal. The weight of the concentrated residue (i.e. high-boiling oligomer) was weighed to find that it was 10.7 wt % per the reaction solution.

Reference Example 3

The reaction was carried out in a batch manner in a reactor equipped with a stirrer and each supply-inlet for acrolein, methyl mercaptan, and a mixture of allylamine/acetic acid. The reactor was charged with 122 g of acrolein (purity: 92 wt %, 2.00 mol), 93.4 g of methyl mercaptan (1.94 mol), and 0.159 g of a mixture of allylamine/acetic acid (molar ratio: 1/1.8, respectively; i.e. allylamine 0.97 mmol/acetic acid 1.73 mmol). The reaction mixture was stirred at 40-70° C. for 30 minutes, and the resultant solution was distilled (20 torr, 70-120° C.) to obtain 3-(methylthio)propanal. The weight of the concentrated residue (i.e. high-boiling oligomer) was weighed to find that it was 6.9 wt % per the reaction solution.

Reference Example 4

The reaction was carried out in a batch manner in a reactor equipped with a stirrer and each supply-inlet for acrolein, methyl mercaptan, and a mixture of pyridine/acetic acid. The reactor was charged with 122 g of acrolein (purity: 92 wt %, 2.00 mol), 93.4 g of methyl mercaptan (1.94 mol), and 0.938 g of a mixture of pyridine/acetic acid (molar ratio 1/10, respectively; i.e. pyridine 1.38 mmol/acetic acid 13.8 mmol). The reaction mixture was stirred at 40-70° C. for 30 minutes, and the resultant solution was distilled (20 torr, 70-120° C.) to obtain 3-(methylthio)propanal. The weight of the concentrated residue (i.e. high-boiling oligomer) was weighed to find that it was 2.6 wt % per the reaction solution.

Reference Example 5

The reaction was carried out in the same manner as Reference Example 4 except that 0.911 g of a mixture of pyridine/ acetic acid (molar ratio: 1/13.0, respectively; i.e. pyridine 1.06 mmol/acetic acid 13.8 mmol) was used instead of 0.938 g of the mixture of pyridine/acetic acid (molar ratio 1/10, respectively). The resultant residue (i.e. high-boiling oligomer) was 5.2 wt %.

Reference Example 6

The reaction was carried out in the same manner as Reference Example 4 except that 0.233 g of a mixture of pyridine/ acetic acid (molar ratio: 1/1.5, respectively; i.e. pyridine 1.38 mmol/acetic acid 2.07 mmol) was used instead of 0.938 g of the mixture of pyridine/acetic acid (molar ratio: 1/10, respectively). The resultant residue (i.e. high-boiling oligomer) was 8.3 wt %.

Reference Example 7

The reaction was carried out in a batch manner in a reactor equipped with a stirrer and each supply-inlet for acrolein, methyl mercaptan, and a mixture of triisobutylamine/acetic acid. The reactor was charged with 122 g of acrolein (purity: 92 wt %, 2.00 mol), 93.4 g of methyl mercaptan (1.94 mol), and 1.08 g of a mixture of triisobutylamine/acetic acid (molar ratio: 1/10, respectively; i.e. triisobutylamine 1.38 mmol/ acetic acid 13.8 mmol). The reaction mixture was stirred at 40-70° C. for 30 minutes, and the resultant solution was distilled (20 torr, 70-120° C.) to obtain 3-(methylthio)propanal. The weight of the concentrated residue (i.e. high-boiling oligomer) was weighed to find that it was 3.5 wt % per the reaction solution.

Reference Example 8

The reaction was carried out in the same manner as Reference Example 7 except that 0.455 g of a mixture of triisobutylamine/acetic acid (molar ratio: 1/2.4, respectively; i.e. triisobutylamine 1.38 mmol/acetic acid 3.31 mmol) was used instead of 1.08 g of the mixture of triisobutylamine/acetic acid (molar ratio: 1/10, respectively). The resultant residue (i.e. high-boiling oligomer) was 5.6 wt %.

The invention claimed is:

1. A process for preparing 3-(methylthio)propanal which comprises reacting acrolein and methyl mercaptan in the presence of a compound of Formula (I):

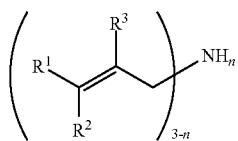

(I)

wherein $R^1$, $R^2$ and $R^3$ are independently selected from the group consisting of hydrogen atom and an alkyl group having 1 to 4 carbon atoms, and n is an integer of 1 or 2 and a compound of Formula (II):

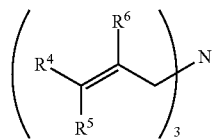

(II)

wherein $R^4$, $R^5$, and $R^6$ are independently selected from the group consisting of hydrogen atom and an alkyl group having 1 to 4 carbon atoms.

2. The process of claim 1 wherein an organic acid is further present in the reaction of acrolein and methyl mercaptan.

3. The process of claim 2 wherein the amount of the compound of Formula (II) is 0.01 to 1.0 mol per 1 mol of the organic acid.

4. The process of any one of claims 1 to 3 wherein the amount of the compound of Formula (I) is 0.001 to 0.50 mol per 1 mol of the compound of Formula (II).

5. The process of claim 1 wherein the amount of the compound of Formula (II) is 0.1 to 2.0 mmol per 1 mol of methyl mercaptan.

6. The process of claim 1 wherein the reaction is carried out while supplying acrolein; methyl mercaptan; and a mixture of the compound of Formula (I), the compound of Formula (II) and the organic acid to the reaction system.

\* \* \* \* \*